US012239288B2

(12) United States Patent
Antonioli

(10) Patent No.: US 12,239,288 B2
(45) Date of Patent: Mar. 4, 2025

(54) APPARATUS AND METHOD FOR MONITORING DIFFERENTIAL PRESSURE

(71) Applicant: Hilary C. Antonioli, Novi, MI (US)

(72) Inventor: Hilary C. Antonioli, Novi, MI (US)

( * ) Notice: Subject to any disclaimer, the term of this patent is extended or adjusted under 35 U.S.C. 154(b) by 348 days.

(21) Appl. No.: 17/646,507

(22) Filed: Dec. 30, 2021

(65) Prior Publication Data

US 2022/0117471 A1     Apr. 21, 2022

Related U.S. Application Data

(63) Continuation-in-part of application No. 15/924,505, filed on Mar. 19, 2018, now Pat. No. 11,253,140.

(60) Provisional application No. 62/474,648, filed on Mar. 22, 2017.

(51) Int. Cl.
*A61B 1/00*     (2006.01)
*G01M 3/32*     (2006.01)
*A61B 90/00*    (2016.01)

(52) U.S. Cl.
CPC ...... *A61B 1/00142* (2013.01); *A61B 1/00055* (2013.01); *A61B 1/00057* (2013.01); *G01M 3/3263* (2013.01); *A61B 2090/064* (2016.02); *A61B 2090/0809* (2016.02)

(58) Field of Classification Search
CPC ............ A61B 1/00016; A61B 1/00018; A61B 1/00055; A61B 1/00057; A61B 1/00128; A61B 1/00131; A61B 1/00142; A61B 2090/064; A61B 2090/0809; A61B 2562/0247; A61B 2562/029; A61B 1/00039; A61B 1/0004; A61B 1/00042; A61B 1/015; G01M 3/26
See application file for complete search history.

(56) References Cited

U.S. PATENT DOCUMENTS

| 4,506,544 A * | 3/1985 | Shimizu | A61B 1/00057 |
| | | | 73/45.5 |
| 2001/0032494 A1* | 10/2001 | Greszler | A61B 1/125 |
| | | | 73/40 |
| 2006/0252991 A1* | 11/2006 | Kubach | G01M 3/26 |
| | | | 600/118 |
| 2013/0008233 A1* | 1/2013 | Kosugi | A61B 1/00128 |
| | | | 73/40.5 R |

(Continued)

*Primary Examiner* — Aaron B Fairchild
*Assistant Examiner* — Stephen Floyd London
(74) *Attorney, Agent, or Firm* — William J. Clemens; Shumaker, Loop & Kendrick, LLP

(57) ABSTRACT

A pressure monitoring device used to monitor for leaks in a tool such as a medical endoscope. The device includes a housing having an internal volume fluidically coupled with an internal volume of the tool to form a combined internal volume. A pump changes the pressure inside the combined internal volume thereby establishing a baseline pressure at a pressure differential from the ambient environment. During operation of the tool, the pressure inside the combined internal volume is monitored for a change exceeding a predefined limit and such a change results in the device issuing an alarm signal indicating a leak has occurred in the tool. The device housing can be directly mounted to the tool, located remotely and connected with a coupling hose, or integrated with an accessory device connected to the tool. Preferably, the pressure differential is negative relative to ambient when the tool is a medical endoscope.

15 Claims, 12 Drawing Sheets

(56) References Cited

U.S. PATENT DOCUMENTS

| | | | |
|---|---|---|---|
| 2016/0081531 A1* | 3/2016 | Yoshie | A61B 1/00059 |
| | | | 73/40 |
| 2017/0027420 A1* | 2/2017 | Choi | G01M 3/26 |
| 2018/0084973 A1* | 3/2018 | Terliuc | A61B 1/00057 |
| 2018/0271356 A1* | 9/2018 | Antonioli | A61B 1/00128 |
| 2020/0000329 A1* | 1/2020 | Sugaya | A61B 1/121 |
| 2020/0022561 A1* | 1/2020 | Hopkins | A61B 1/00055 |
| 2020/0229682 A1* | 7/2020 | Iikura | A61B 1/00055 |
| 2020/0337527 A1* | 10/2020 | Moritomo | A61B 1/00119 |

\* cited by examiner

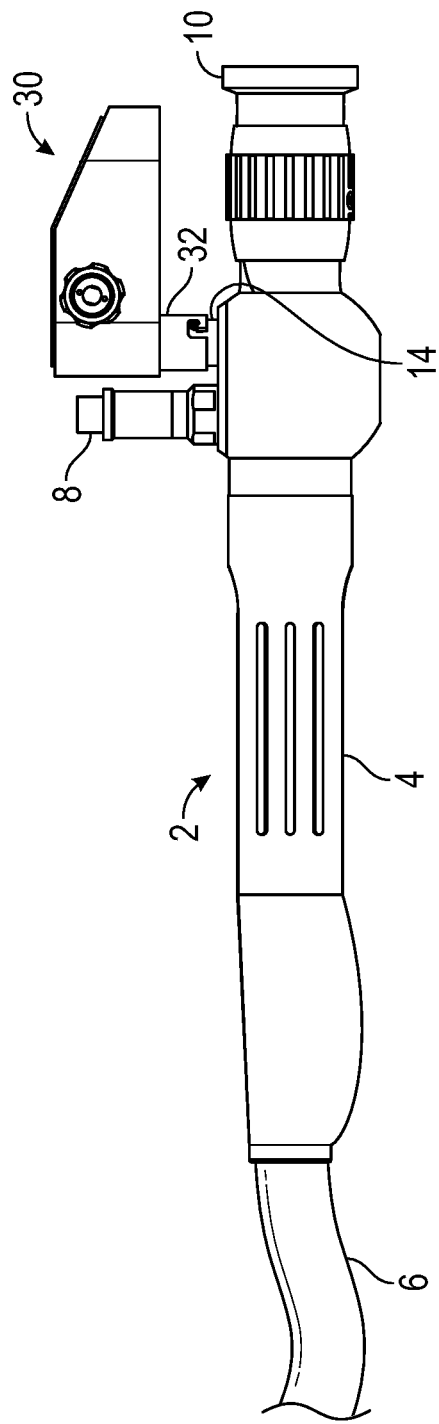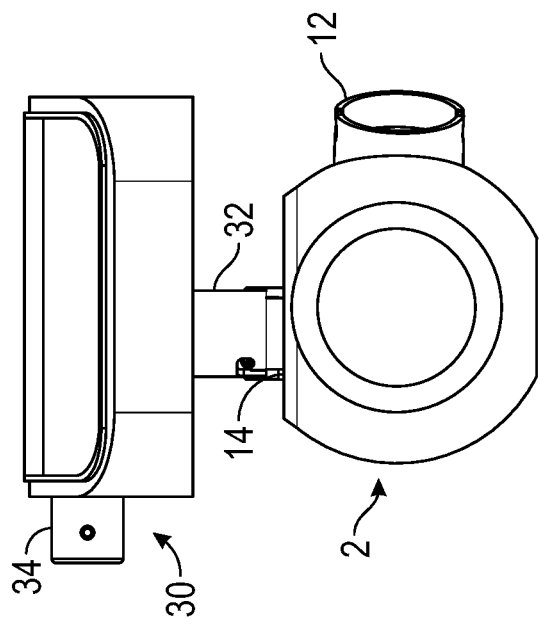
FIG. 1C
FIG. 1D

APPARATUS AND METHOD FOR MONITORING DIFFERENTIAL PRESSURE

CROSS-REFERENCE TO RELATED APPLICATIONS

This application is a continuation-in-part of the co-pending U.S. patent application Ser. No. 15/924,505 filed Mar. 19, 2018 and claims the benefit of the priority date of U.S. Provisional Patent Application Ser. No. 62/474,648, titled APPARATUS AND METHOD FOR MONITORING DIFFERENTIAL PRESSURE, filed Mar. 22, 2017.

FIELD OF THE INVENTION

This present disclosure relates generally to a pressure monitoring device coupled to a closed-cavity tool and, more particularly, to an apparatus and a method for monitoring pressure to detect a leakage-type failure of a medical device such as an endoscope by creating and monitoring a differential pressure to the external atmospheric pressure.

BACKGROUND OF THE INVENTION

An endoscope is an illuminated optical, typically slender and tubular instrument used to look deep into the body and used in a procedure called an endoscopy. Different types of endoscopes have been developed to be used in different parts of the body—such as the esophagus, the colon, and other places. Endoscopes serve a valuable function, allowing doctors to visualize internal parts of the body without surgical incision, and further allowing the collection of tissue specimens (biopsies) for testing. As a result of the biopsy testing and visual information collected, the doctor can determine an appropriate course of treatment for the patient.

The entirety of an endoscope—including a structural body at the proximal end (in the doctor's hand) and the flexible tubular distal portion—is closed, forming a sealed internal volume. The formation of a puncture or leak at any location in the endoscope—particularly in the tubular portion which has been inserted into the patient—would allow the patient's bodily fluids to enter the internal volume of the endoscope, and allow any material inside the endoscope to escape into the patient's body. Because it is impossible to guarantee that the interior of an endoscope is sterile, especially after multiple usages, it is most desirable to avoid such leakage.

By definition, a leaking endoscope cannot be effectively sterilized or high-level disinfected, and would never knowingly be used on a patient. Medical service providers typically leak-test endoscopes after the scope is used in one procedure and before the scope is used in another procedure. However, if cleaning and sterilization is undertaken with a leak present, the interior of the endoscope can be flooded with cleaning fluids or other chemicals, resulting in a much higher repair cost. Additionally, if the leak is left undetected and the endoscope is used in a procedure, the patient could be exposed to the chemicals or other harmful substances. Therefore, there is a need for real-time endoscope leak testing during a procedure so that, if a leak is detected, the doctor can terminate the procedure and remove the endoscope from the patient as quickly as practicable.

BRIEF SUMMARY OF THE INVENTION

In accordance with the teachings of the present disclosure, a pressure monitoring control module is provided for use with a tool such as a medical endoscope. In a first embodiment, the control module includes a housing that is fluidically and releasably coupled with an internal volume of the endoscope. A pump is used to change the pressure inside the device housing and endoscope, thereby establishing a pressure differential from the ambient environment. During an endoscopy procedure, the pressure inside the device housing is monitored, and a change in pressure exceeding a predefined limit causes an alarm signal indicating a leak has occurred in the endoscope. In the first embodiment, the device housing forms a combined volume with the endoscope internal volume and can be directly mounted to the endoscope, or located remotely and connected with a coupling tube. The pump can be integrated internally to the device housing, or it can be a separate external pump that is connected to the housing. The pressure differential in the combined volume can be positive or negative relative to ambient.

In a second embodiment, a pressure chamber in the device housing forms the combined volume with the endoscope internal volume. The leak-detecting apparatus monitors a differential pressure in the endoscope during use to perform a medical procedure. The housing has an outlet port adapted for coupling the housing to the endoscope such that the internal volume of the endoscope is in fluid communication with the internal volume in the housing. A pump in the housing changes air pressure inside the combined internal volume to establish a baseline pressure inside the combined internal volume that is different from an ambient pressure outside the endoscope. A pressure sensor inside the housing monitors the pressure in the combined internal volume and a processor in the housing is configured to establish the baseline pressure using the pump, to monitor the air pressure inside the combined volume using the pressure sensor, and to issue an alarm signal indicating a possible leak in the endoscope if the air pressure inside the combined volume changes from the baseline pressure by more than a threshold amount or a rate of change of the air pressure inside the combined volume exceeds a rate threshold.

The baseline pressure preferably is lower than the ambient pressure outside the endoscope, but could be higher. The alarm signal is a visual signal provided by an alarm visible on an outside surface of the housing, an audible signal, or a combination of audible and visual signals, and the alarm signal can be cancelled or silenced by a user input to the processor.

The device according to the second embodiment includes a humidity sensor or a moisture sensor inside the housing and wherein an alarm signal is issued from the alarm upon detection of moisture or a change of humidity in the combined internal volume. At least one communication channel is provided enabling electronic communication between the processor and a computer providing supervisory control of the tool, where the communication channel is hardwired or wireless communication.

A method according to the invention for detecting a leak in a closed-cavity tool during operation of the tool comprises the steps of: providing a differential pressure monitoring control module; releasably coupling the control module to the tool such that an internal volume of the tool is in fluid communication with an internal volume in the control module thereby forming a combined internal volume; changing an air pressure inside the combined internal volume to establish a baseline pressure inside the combined internal volume which is different from an ambient pressure outside the tool; monitoring the air pressure inside the combined volume during operation of the tool using a pressure sensor connected to a processor in the control module; and issuing an alarm signal indicating a possible leak in the tool if the air pressure inside the combined volume changes from the baseline pressure by more than a threshold amount or a rate of change of the air pressure inside the combined volume exceeds a rate threshold.

The method further includes at least one of: signaling to a user of the tool when the baseline pressure is established; wherein the established baseline pressure inside the combined internal volume is lower or higher than the ambient pressure outside the tool; monitoring a humidity inside the combined internal volume and signaling to a user of the tool when the humidity differs from a baseline humidity previously measured in the combined internal volume; mounting the control module upon the tool and coupling an outlet port of the control module to an inlet port of the tool to form the combined volume; positioning the control module remotely from the tool and coupling an outlet port of the control module to an inlet port of the tool with a hose to form the combined volume; including operating a valve connected between a pump in the control module and the internal volume of the tool to establish fluid communication between the pump and the combined internal volume during the changing of the air pressure inside the combined internal volume by the pump and to block fluid communication between the pump and the combined internal volume during the operation of the tool; and wherein the valve is connected between the pump and an inlet to a pressure chamber in the control module, the pressure chamber having an outlet releasably coupled to the internal volume of the tool to form the combined internal volume.

An advantageous embodiment of the method according to the invention is used for detecting a leak in a medical endoscope during operation of the endoscope to perform a medical procedure, the method comprising the steps of: providing a differential pressure monitoring control module; releasably coupling the control module to the endoscope such that an internal volume of the endoscope is in fluid communication with an internal volume in the control module thereby forming a combined internal volume; changing an air pressure inside the combined internal volume to establish a baseline pressure inside the combined internal volume which is lower than an ambient pressure outside the endoscope; monitoring the air pressure inside the combined volume during operation of the endoscope to perform the medical procedure using a pressure sensor connected to a processor in the control module; and issuing an alarm signal indicating a possible leak in the endoscope if the air pressure inside the combined volume changes from the baseline pressure by more than a threshold amount or a rate of change of the air pressure inside the combined volume exceeds a rate threshold.

This method further comprises at least one of: signaling to a user of the endoscope when the baseline pressure is established; the established baseline pressure inside the combined internal volume is lower than the ambient pressure outside the endoscope; monitoring a humidity inside the combined internal volume and signaling to a user of the endoscope when the humidity differs from a baseline humidity previously measured in the combined internal volume; positioning the control module remotely from the endoscope and coupling an outlet port of the control module to an inlet port of the endoscope with a hose to form the combined volume; and operating a valve connected between a pump in the control module and the internal volume of the endoscope to establish fluid communication between the pump and the combined internal volume during the changing of the air pressure inside the combined internal volume by the pump and to block fluid communication between the pump and the combined internal volume during the operation of the endoscope, and wherein the valve is connected between the pump and an inlet to a pressure chamber in the control module, the pressure chamber having an outlet releasably coupled to the internal volume of the endoscope to form the combined internal volume.

Additional features of the presently disclosed methods and devices will become apparent from the following description and appended claims, taken in conjunction with the accompanying drawings.

BRIEF DESCRIPTION OF THE DRAWINGS

FIG. 1C is a side elevation view of the endoscope with the control module shown in FIG. 1A;

FIG. 1D is an end view of the endoscope with the control module shown in FIG. 1A;

DETAILED DESCRIPTION OF THE INVENTION

The following discussion of the embodiments of the disclosure directed to an apparatus and method for monitoring differential pressure is merely exemplary in nature, and is in no way intended to limit the disclosed devices or their applications or uses. For example, the invention is described in the context of an endoscope, but is anticipated to be useful with tools of many types. In respect of the methods disclosed, the steps presented are exemplary in nature, and thus, steps can be added, removed or reordered without departing from the spirit and scope of the invention.

As discussed above, there is a need for real-time endoscope leak testing during a procedure so that, if a leak is detected, the doctor can terminate the procedure and remove the endoscope from the patient as quickly as practicable. Applicant is not aware of any FDA (Food and Drug Administration) approved devices for leak testing an endoscope during use on patients or any standard for testing endoscopes for leaks during use on patients. Thus, patients are at risk during medical procedures using an endoscope. The apparatus according to the invention uses an innovative means of detecting failure of a tool, such as a medical endoscope, by creating and monitoring a differential pressure to the external atmospheric (ambient) pressure. After the differential pressure is established, any significant change to the fluid/gas pressure inside the endoscope indicates a leak has developed and a cross contamination potential exists, and the monitoring device immediately notifies the person or system operating the tool of the potential problem. The indication can be any form of light, sound, electronic communication or otherwise.

Two main embodiments of the invention are disclosed below. The first embodiment can be a passive device that does not include a built-in means for establishing a pressure differential between the interior of the endoscope and the environment. The passive device must be attached to an external pump which creates the pressure differential. An active version of first embodiment of the device includes an integral internal piston assembly and a power source, and can create the desired pressure differential without the need for connecting to an external pump. Either the passive device or the active device can further be configured to be directly mounted in or on the endoscope, or located remotely from the endoscope and connected by a small tube or hose.

Figure 6:
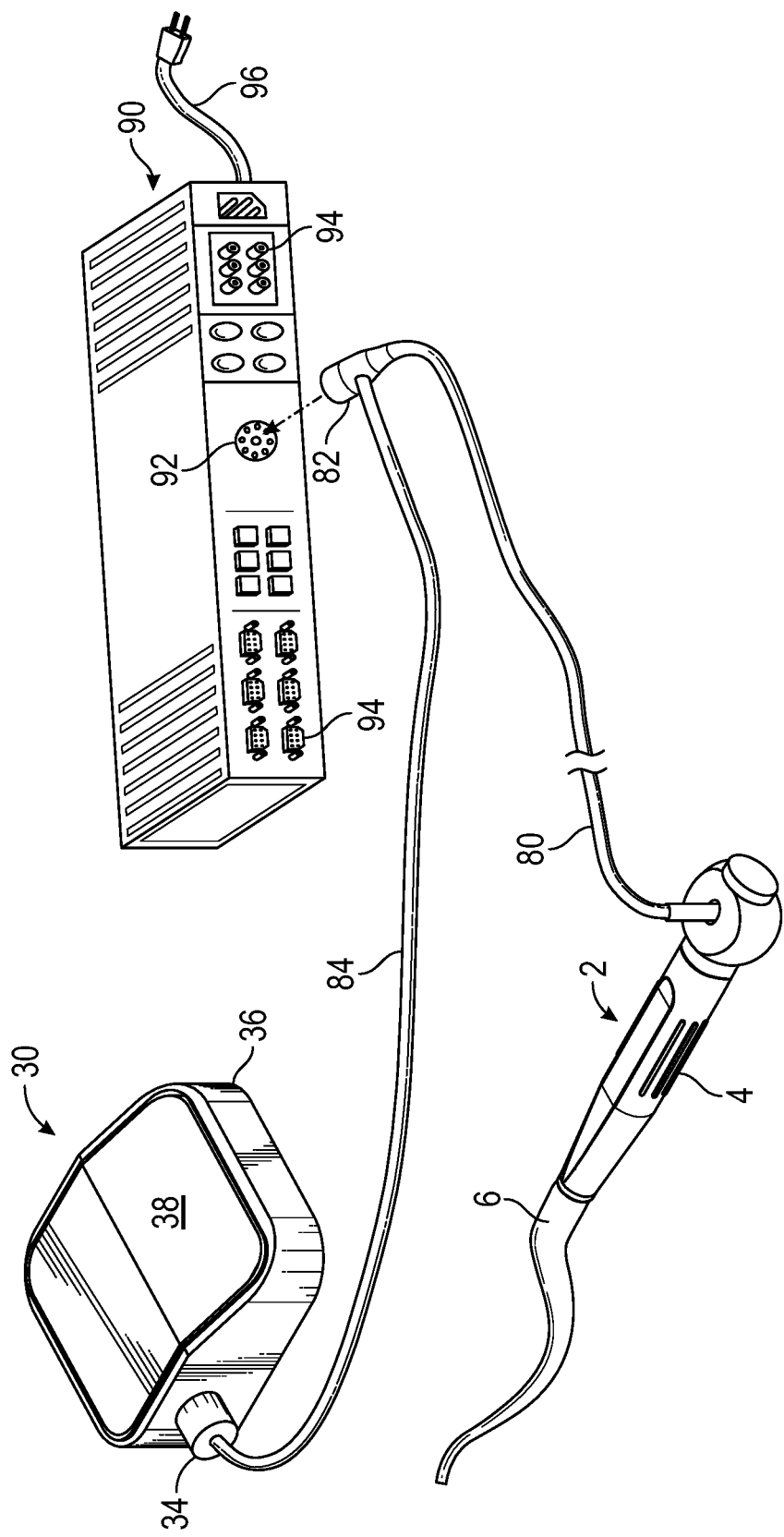
FIG. 6 is an illustration of a pressure monitoring control module located remotely from the endoscope and connected to the endoscope by a hose.

There is shown in FIGS. 1A-1D a tool 2 to which a pressure monitoring control module 30 according to the invention is mounted. In FIGS. 1 and 6, and all of the following discussion, the tool 2 is specifically an endoscope. The tool 2 includes a body 4, which is a structural component made of a suitable metal or plastic. The body 4 is generally tubular and hollow. At a distal end of the body 4, meaning the end of the body 4 which is situated away from the doctor, is affixed a flexible tube 6. The tube 6 is the component of the tool 2 that is inserted into the patient—for example, down the esophagus toward the stomach. The tube 6 is much longer than shown in the figures as its detail is not significant to the discussion, other than to point out that the distal end of the tube 6 is sealed, such as with a lens through which fiber optic elements can illuminate and view, or a video camera element.

The endoscope (tool 2) shown in FIG. 1 is an optical endoscope, with an eyepiece and fiber optics (discussed below) for illumination and viewing. Another type of endoscope, which is increasing in popularity, is a video endoscope (discussed later in reference to FIG. 6). In a video endoscope there is no eyepiece; instead, a digital video camera is located at the distal end of the flexible tube 6, and digital video images are provided by electrical/electronic connection to an external video processor for display on a display device. The disclosed leak testing technique using the control module 30 is applicable to both optical and video endoscopes.

At a location near the middle of the body 4, an adapter 8 is provided, where the adapter 8 is configured for attachment of a light source to provide illumination via light fibers into the body cavity being examined. At a proximal end of the body 4, an eyepiece 10 is provided, where the eyepiece 10 allows attachment of a video camera or other means of viewing the body cavity via optical fibers that extend all the way to the distal end of the flexible tube 6. The tool 2 also includes a port 12 configured to accept a biopsy tool (not shown), where the port 12 provides access to a secondary internal tubular passage (not shown) through which the biopsy tool can be extended to the distal end of the flexible tube 6 to take a tissue sample from the patient.

The above discussion of the tool 2 (endoscope) is provided for background information only. The main point is that the body 4 and the flexible tube 6 are sealed at both ends and at all other ports, resulting in an internal volume that should be leak-free and airtight at all times. Thus, only exterior surfaces of the tool 2 should ever be in contact with the patient, and only those exterior surfaces can be and must be sterilized or high-level disinfected before a procedure.

As discussed above, it is undesirable for a leak to develop in the tool 2 during a patient procedure. However, it can easily be imagined that a leak or puncture could occur, in the flexible tube 6 for example, during a procedure. It is even more undesirable for a leak to develop and go undetected, as the continued use of the tool 2 exposes the patient to greater potential cross contamination with material inside the tool 2. Until now, doctors had no way to determine if a leak had developed during a procedure. Current devices used to leak test an endoscope are designed to test the instrument prior to cleaning for subsequent use.

The pressure monitoring control module 30 provides the leak detection capability discussed above. The control module 30, shown without the tool 2 in FIGS. 2A-2E, is in fluid communication with the internal volume of the tool 2 through an outlet port 32 (FIG. 2A) which is releasably coupled to a corresponding pressure port 14 on the body 4 of the tool 2 (FIG. 1C). When the control module 30 is coupled to the tool 2, this causes the internal pressures to become equal but unknown relative to the atmospheric pressure outside the tool 2 and control module 30. A pumping device (not shown) is then connected to an accessory port 34 (FIGS. 2A-2C) of the control module 30. After the pumping device is activated, the pressure inside the control module 30 and the tool 2 is changed to a pressure at the desired difference relative to atmospheric pressure. At this point, a signal is provided to indicate that the desired differential pressure has been established and leak detection capability is operational via pressure monitoring.

The differential pressure of the combined internal volume (of the control module 30 and the tool 2) relative to ambient can be positive or negative. In other words, the combined internal volume can be pressurized slightly, or the combined internal volume can be pumped out to a partial vacuum. In a preferred embodiment, the pressure differential is a partial vacuum in the combined internal volume of the control module 30 and the tool 2, and the pressure difference is about ⅓ of atmospheric pressure. In other words, if the ambient pressure in the procedure room is a standard atmosphere of 14.7 psi, then the absolute pressure in the combined internal volume will be established at about 10 psi (which is about ⅓ less than 14.7). Once the desired pressure differential is established, the pumping device is turned off and the pressure in the combined internal volume should remain at the desired value as long as there are no leaks. The 10 psi is an example and, as explained above, the pressure differential can be any selected value above or below ambient.

By establishing the differential pressure as described above, any leak or puncture in the tool 2 will immediately be made apparent by a change in the pressure in the combined internal volume. In the example described above, where the combined internal volume of the control module 30 and the tool 2 has an initial absolute pressure of 10 psi, if a leak develops in the tool 2, the pressure in the control module 30 will rise from 10 psi to near ambient pressure of 14.7 psi. During pressure monitoring, some slight variation from the 10 psi value is allowable without signaling an alarm, to account for temperature change of the flexible tube 6 when inserted into the patient, for example. However, any increase in pressure greater than about 10%, or 1 psi, for example, can be considered a definite indication of a leak. The value of the pressure change that triggers an alarm is freely selectable. This pressure monitoring leak detection technique is only effective when a differential pressure is first established, as in the embodiments of the present invention.

Any suitable design for the control module 30 can be used, as long as the device is airtight and capable of monitoring a change in internal pressure. The control module 30 as shown in FIGS. 2A-2E has a case 36 or bottom portion that is cup-shaped and covered by a top 38 to form an enclosed housing for components. The interior of the enclosed housing forms a pressure chamber defining the internal volume of the control module 30. The accessory port 34 and the outlet port 32 extend through the walls of the case 36, allowing fluid communication with the pumping device and the tool 2, respectively.

Figure 1A:
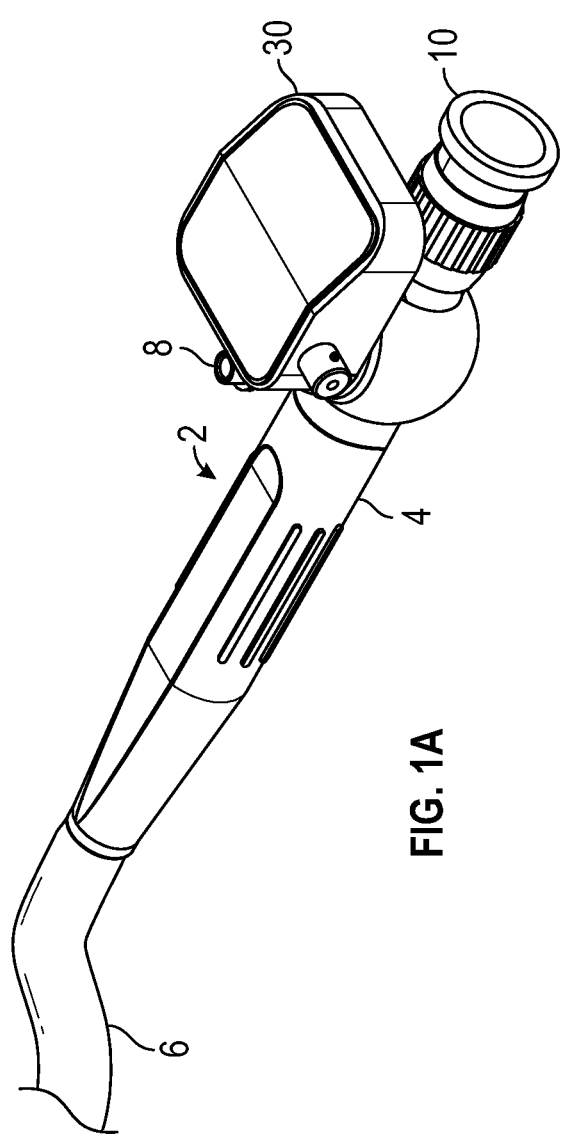
FIG. 1A is a perspective view illustration of an endoscope having a pressure monitoring control module according to a first embodiment of the invention mounted thereon.
Figure 1B:
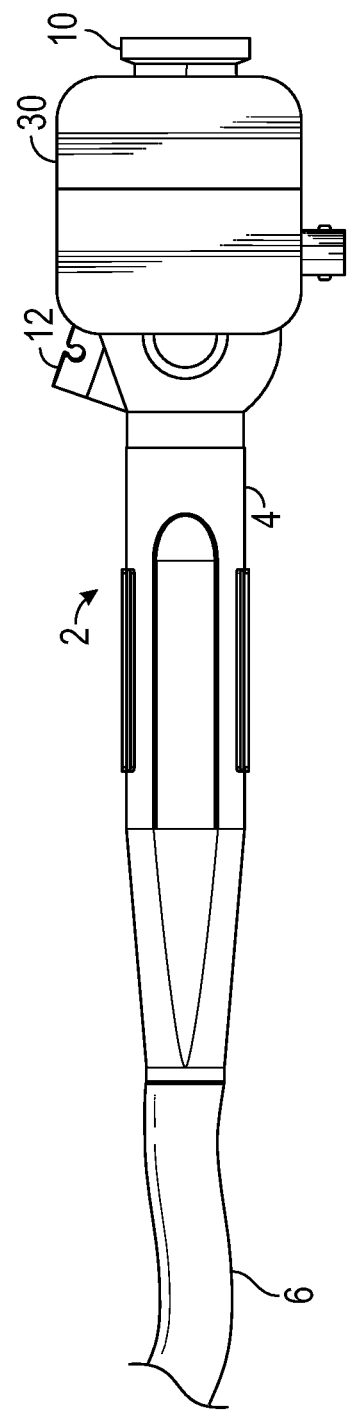
FIG. 1B is a top plan view of the endoscope with the control module shown in FIG. 1A.
Figure 2A:
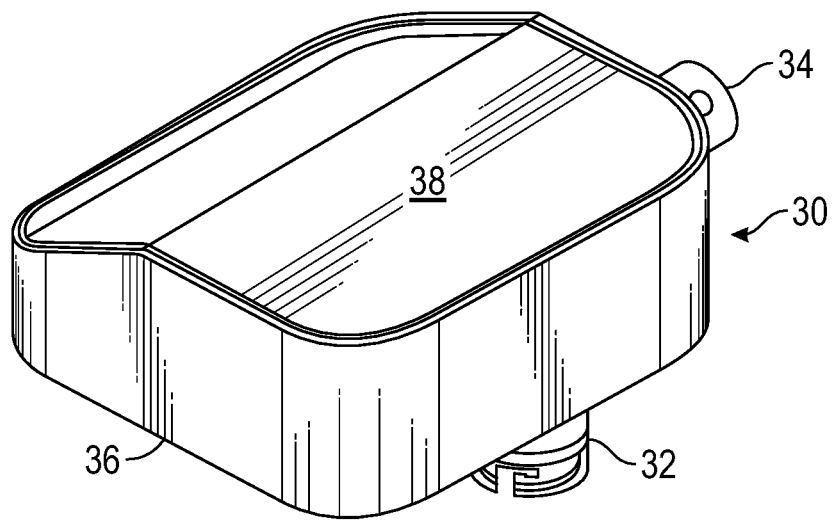
FIG. 2A is a perspective view illustration of the pressure monitoring control module shown in FIG. 1A.
Figure 2B:
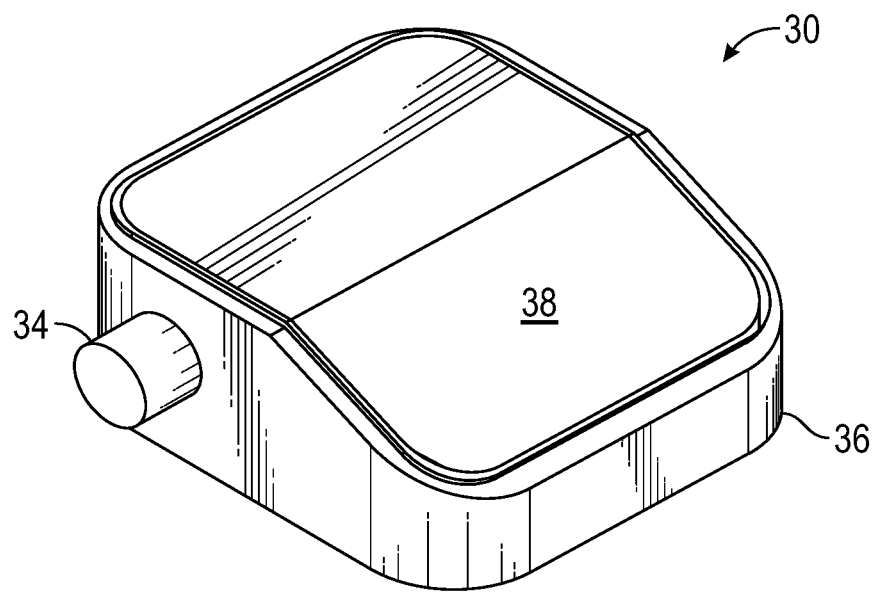
FIG. 2B is a reverse perspective view of the control module shown in FIG. 2A.
Figure 2C:
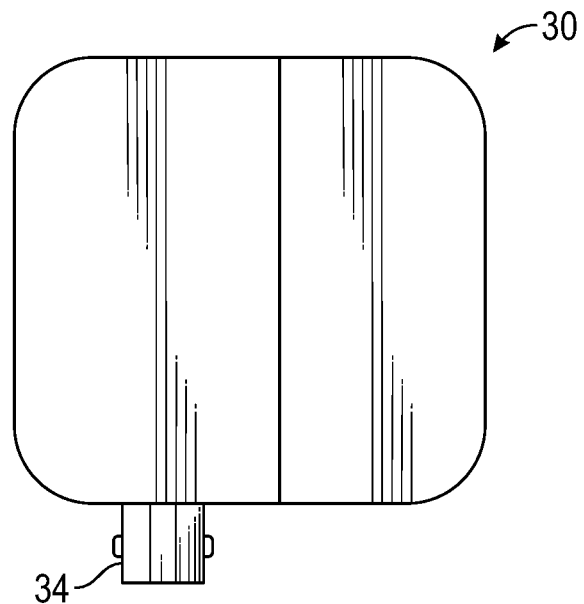
FIG. 2C is a top plan view of the control module shown in FIG. 2A.
Figures 2D, 2E:
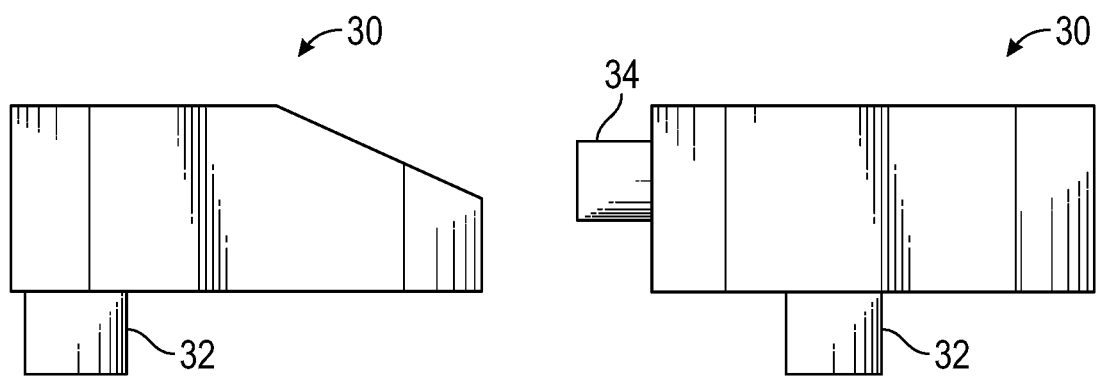
FIG. 2D is a side elevation view of the control module shown in FIG. 2A.
FIG. 2E is an end view of the control module shown in FIG. 2A.
Figure 3A:
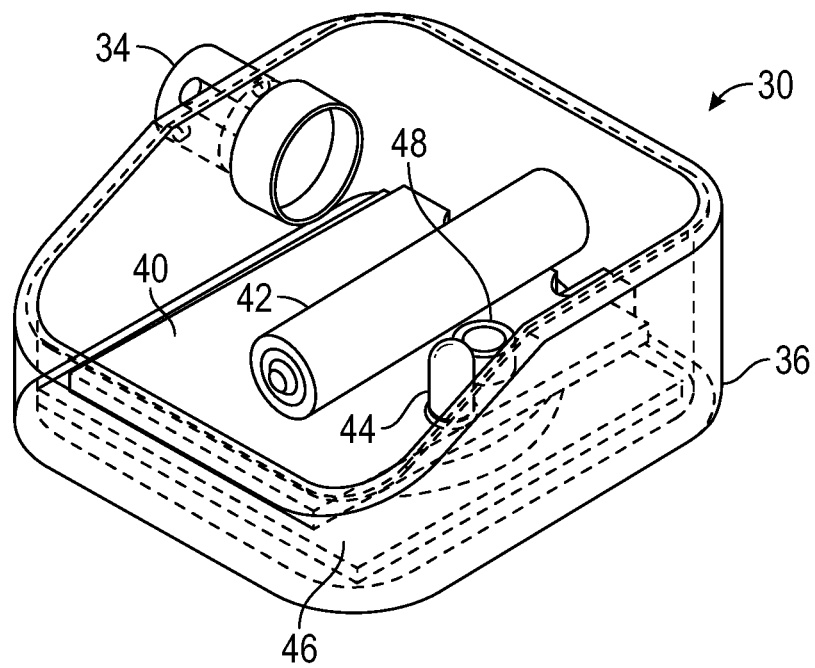
FIG. 3A is a cutaway perspective view similar to FIG. 2A of a first embodiment of the pressure monitoring control module.
Figure 3B:
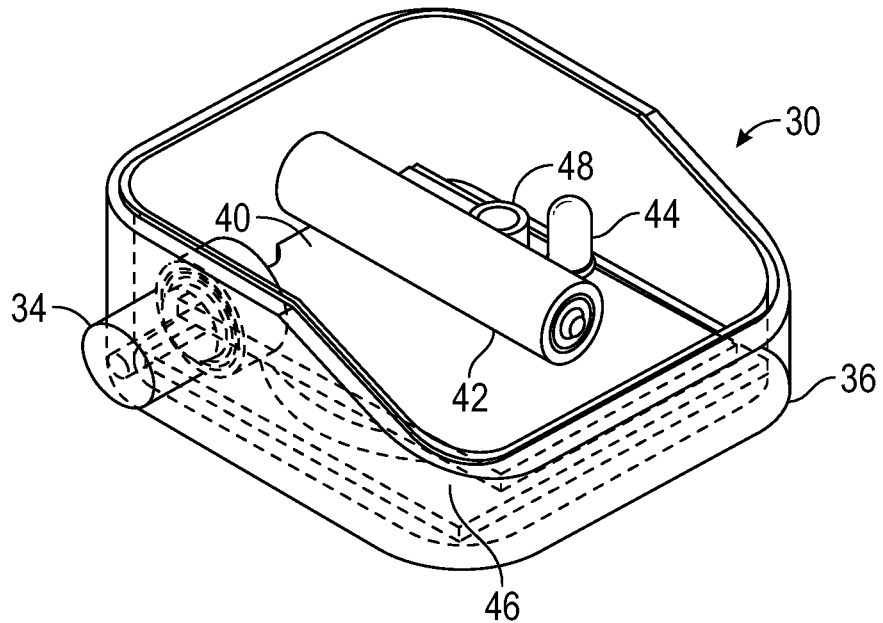
FIG. 3B is a reverse cutaway perspective view of the control module shown in FIG. 3A.

The components inside the housing of the first or passive version of the control module 30 are shown in FIGS. 3A and 3B. A printed circuit board (PCB) 40 is positioned in the bottom of the case 36. The PCB 40 is an exemplary representation for any suitable type of processor that can be used in the control module 30. Instead of the PCB 40, an application specific integrated circuit (ASIC), a general purpose microprocessor, or any other suitable processing or computing device can be used. Mounted on or connected to the PCB 40 are a battery 42, an LED 44, an optional wireless charging coil 46 and a pressure sensor module 48. The battery 42 provides power to the components in the control module 30—including the PCB 40, the LED 44 and the pressure sensor module 48. The LED 44 is representative of any suitable visual signal generating device such as an LCD or touchscreen.

The LED 44 is an indicator that provides communication to the operator through different output states. The LED 44 is representative of any and all types of outputs that can be desired from the control module 30. The outputs can be any modality or combination of modalities: optical (such as by the LED 44); audible; wirelessly transmitted; or hard wired. Optical and audible outputs can be provided directly by the control module 30. Output signals can also be provided from the control module 30 to a monitoring system that is in use in the procedure room. That is, the monitoring system in the procedure room would typically have its own built-in data recording system, audible alarms, visible alarms, etc. Outputs from the control module 30 would be compatible with and usable as inputs to the procedure room monitoring system.

To use the control module 30 for leak detection by pressure monitoring and/or other monitoring (humidity, moisture, etc.), the control module 30 is first coupled to the tool 2 as described above. Then the pumping device is activated to create the differential pressure between the combined internal volume (of the module 30 and the tool 2) and the outside environment, as discussed above. When an acceptable internal pressure (such as 10 psi absolute) is reached, the LED 44 displays a signal, such as a green light, indicating the acceptable differential pressure. Once set, the LED 44 will continue to display the signal indicating proper tool pressure. If the sensed pressure changes outside set limits, then the LED 44 signals an alarm condition indicating a change in pressure and a possible leak in the tool 2. As mentioned, the "operative/normal" signal and the "alarm" signal can be displayed by the LED 44, produced audibly by the control module 30, and/or provided by electronic communication from the control module 30 to the procedure room monitoring system including a monitor being viewed by the physician performing the procedure.

The pressure sensor module 48 monitors pressure continuously when the control module 30 is in operation—first determining when the acceptable pressure differential has been established, and then monitoring the internal pressure to detect changes. In monitoring mode, the control module 30 allows for some variations in the pressure signal from the pressure sensor module 48 without setting off the alarm signal. The normal acceptable pressure variations can be due to temperature changes in the tool 2 when advanced into the patient's body, and slight volume changes caused by bending and unbending of the flexible tube 6 of the tool 2. The control module 30 triggers the alarm should the pressure change too quickly or outside preset parameters. For example, if the internal pressure climbs from the 10 psi starting value, the alarm can be triggered when the internal pressure reaches a threshold value of 11 psi.

Rate of pressure change is also monitored and can trigger an alarm, where the rate of pressure change detection allows for the possibility of contamination plugging a leak prior to the internal pressure reaching the alarm threshold. For example, if the internal pressure climbs from 10 psi to 10.8 psi within a few seconds, the alarm can be triggered due to the high rate of pressure change, even though the alarm pressure threshold (e.g., 11 psi) is not exceeded because the leak is temporarily plugged by a contaminant.

When a leak is detected and the alarm is triggered, the control module 30 can be configured to release the differential pressure, so that the interior of the endoscope quickly returns to ambient pressure. Alternately, the control module can not mechanically release the differential pressure, but instead just allow the interior pressure to return to ambient due to the leak. The alarm can be disabled or reset by the operator. Even if the operator decides to immediately discontinue the procedure upon notice of a leak, he or she may not want to continue to hear the alarm signal while removing the endoscope from the patient, so disabling or silencing the alarm is a desirable feature. The operator of the tool 2 may also determine that it would not be desirable to immediately discontinue the procedure, in which case the ability to silence the alarm is even more essential. Any time a leak is detected while the endoscope is inside a patient, the operator can choose to take immediate remedial action with the patient, or make note of follow-up action or monitoring which is to be undertaken.

The control module 30 also provides the option to re-establish the pressure differential and restart leak detection monitoring. In this case, the pumping device would again be activated to create the differential pressure between the combined internal volume (of the module 30 and the tool 2) and the outside environment, as discussed above. Upon signaling that the desired differential pressure has been achieved, the procedure can resume with active leak detection monitoring, and the operator can choose to continue or discontinue the procedure based upon how soon a second leak alarm is issued.

Power for the control module 30 is supplied by the battery 42 that is rechargeable through the wireless charging coil 46 when in the presence of an external charging system. In some versions, the control module 30 could be disposable and the wireless charging coil 46 would then not be present. The battery 42 can also be a single-charge disposable type, even if the control module 30 itself is reusable many times; in this case the charging coil 46 is not needed. In another version, an external power supply could provide power to the control module 30 via an electrical cable, and the battery 42 would not be needed for normal operation while serving as a backup power source.

A check valve or shut-off valve can be provided between the external pumping device and the control module 30—near the accessory port 34. The check valve or shut-off valve would prevent pressure leakage through the accessory port 34 after the differential pressure is established and the pumping device is turned off.

Other types of sensors besides the pressure sensor module 48 can also be included in the control module 30. For example, a humidity sensor can be provided inside the control module 30, and a baseline humidity level could be measured once the control module 30 is coupled to the tool 2. Then, during the endoscopic procedure, any significant change in humidity level would trigger the alarm signal indicating a potential leak. A moisture sensor can also be provided, either instead of or in addition to the humidity sensor. It is possible that in some circumstances the humidity sensor, or another type of sensor, can detect a change of conditions inside the control module 30—indicative of a leak in the tool 2—sooner than the pressure sensor module 48.

Figure 4A:
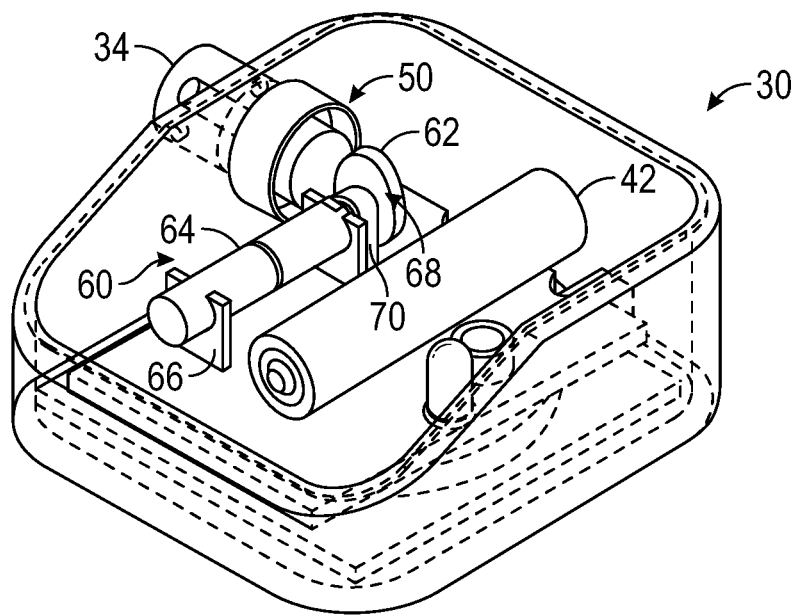
FIG. 4A is a cutaway perspective view similar to FIG. 2A of a second embodiment of the pressure monitoring control module.
Figure 4B:
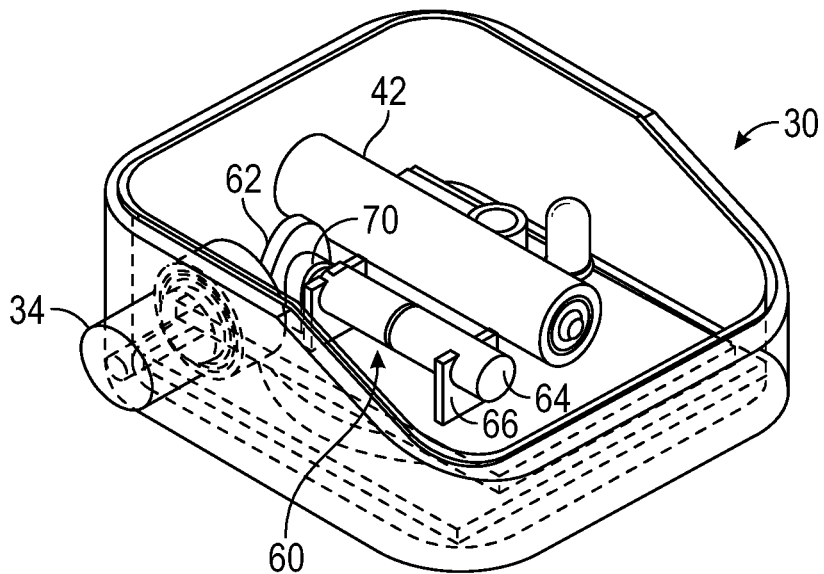
FIG. 4B is a reverse cutaway perspective view of the control module shown in FIG. 4A.
Figure 5:
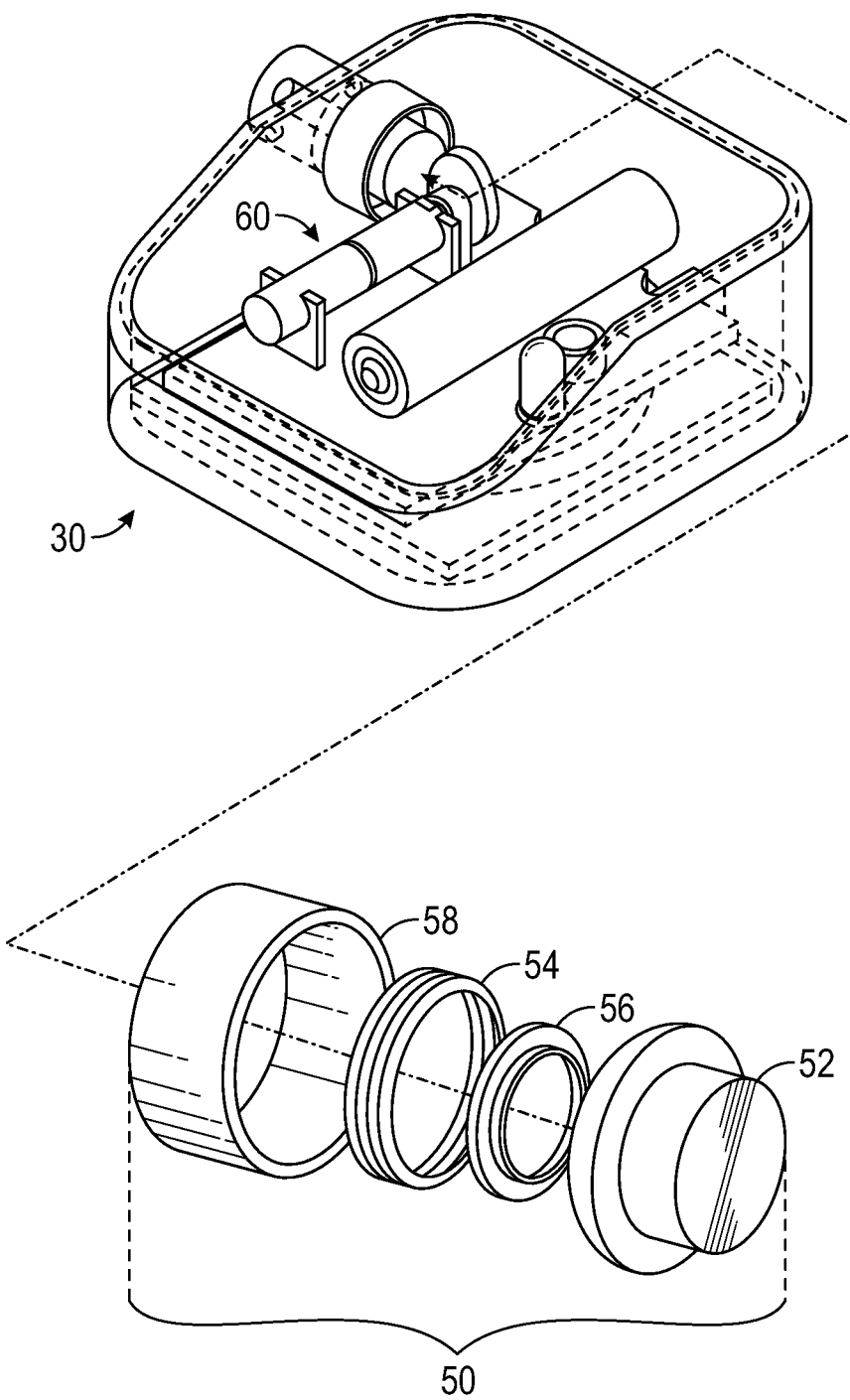
FIG. 5 is an exploded perspective view of the piston assembly in the second embodiment of the control module shown in FIG. 4A.

The second version of the first embodiment of the control module 30 according to the invention is an active embodiment and is shown in FIGS. 4A, 4B and 5. The active device functions identically to the passive device with one exception; an internal piston assembly is added to the active device, thus eliminating the need to connect to an external pumping device as discussed above for the passive device. The addition of the piston assembly in the active device enables the control module 30 to modify the internal pressure to a level different enough to allow sensing of a leak anywhere within the monitored cavities.

The active version of the control module 30 has a pump in the form of a piston assembly 50 that includes a piston 52, a compression spring 54, a check valve 56 and a piston cavity 58. The piston assembly 50 is shown in exploded form in FIG. 5. The control module 30 also has a drive assembly 60 that includes a cam 62, a planetary DC motor 64 and a motor mount 66. The motor 64 rotates an axle 68 in an axle support 70. The cam 62 is attached to the axle 68 for rotation by the motor 64. When the control module 30 is commanded to begin and establish the differential pressure, the motor 64 rotates the axle 68 (and therefore the cam 62) by a quarter turn or a half turn. The non-symmetric form of the cam 62 presses against the piston 52 to move the piston 52. If the piston 52 is moved outward (away from the axle 68) by the cam 62, the volume inside the control module 30 will increase and the pressure inside the control module 30 will drop. If the cam 62 is rotated to allow inward movement of the piston 52, the spring 54 pushes the piston 52 inward to decrease the volume and increase the pressure inside the control module 30. The piston assembly 50 can be configured to increase or decrease internal pressure by selecting the check function of the check valve 56.

The PCB 40 in the control module 30 can be provided with one or more communication components to communicate data and track performance of the tool 2. These communication components can be optical, wired, wireless and/or any other means of communication between two devices. Thus, the components of the control module 30 can send and/or receive signals through the communication component(s) to and from a data processing device such as a computer as would be used in an endoscopy procedure room. This includes the ability to log performance of the tool 2 over a timed interval made retrievable through any of the aforementioned techniques.

While the pressure monitoring control module 30 has been described above and shown in FIGS. 1A-1D as an external tool-mounted configuration, other configurations are possible. In one alternate configuration, the control module 30 can be miniaturized for integrated mounting inside the tool 2, or mounted in an accessory device used with the endoscope. In another configuration, the pressure monitoring control module 30 can be positioned remotely.

FIG. 6 is an illustration of a pressure monitoring control module 30 located remotely from the endoscope tool 2 and connected to the endoscope by fluid couplings discussed below. In FIG. 6, the tool 2 is a video endoscope of the type described earlier. In a typical video endoscope system, the endoscope (tool 2) is connected to a video processor 90 via an umbilical cord 80. The umbilical cord 80 provides electronic communication from the endoscope tool 2 to the video processor 90. The umbilical cord 80 can also include one or more fluid passages used for providing sterile water or other fluids to the distal end of the flexible tube 6.

At an end opposite the tool 2, the umbilical cord 80 terminates in a plug 82, which plugs into a jack 92 on the video processor 90. The video processor 90 also includes one or more ports 94 for communication with a separate computer, a video display device, or other electronic device, as understood by those skilled in the art. The ports 94 can be on an opposite side of the video processor 90 from the jack 92; they are shown on the same side in FIG. 6 for clarity and simplicity. The video processor 90 also includes a power cord 96 for providing electrical power.

The control module 30 depicted in FIG. 6 (shown much larger than scale) is the active device of FIGS. 4 and 5, with its own internal pumping device. A hose 84 releasably couples the accessory port 34 of the control module 30 with the plug 82 on the end of the umbilical cord 80. The differential pressure created by the control module 30 is communicated to the tool 2 via the hose 84 and a continuation of the hose 84 that is inside the umbilical cord 80. The hose 84 can be very small in diameter, as volume flow rate through the hose 84 is not an important factor. An inline filter (not shown, see FIG. 8) can be provided in the hose 84 to prevent contamination of the control module 30 when using a negative differential. In the embodiment of FIG. 6, the tool 2 is not encumbered with any additional structural appendages, thus enabling easy manipulation of the tool 2 by the operator.

In any version, and particularly in the device shown in FIG. 6, the control module 30 can be connected to a procedure room computer system for full two-way electronic communication—including sending signals (ready signal, alarm signal) from the control module 30, sending collected data from the control module 30, and sending signals from the procedure room computer system to the control module 30, such as procedure begin and end signals, silence alarm signal, etc. The two-way communication between the control module 30 and the procedure room computer system can be facilitated by wireless communication or by wires running along the hose 84 to the plug 82 and into the video processor 90. The collected data sent from the control module 30 to the procedure room computer system can include date, start time, stop time, tool ID #, patient identification information, pressure vs. time data, and any other available data. In any of the devices discussed above, the control module 30 can be constructed to be reusable and/or disposable.

The distance between the video processor 90 and the tool 2 as shown in FIG. 6 is not to scale; the video processor 90 would be much farther distant from the tool 2 in relation to the sizes shown; that is, the umbilical cord 80 in reality is longer than shown in FIG. 6. Another configuration of the device shown in FIG. 6 would incorporate the control module 30 into the video processor 90. This would allow the hose 84 to be eliminated or greatly reduced in length, and the fluid communication between the control module and the endoscope would be directly through the umbilical cord 80 and the plug 82 to the jack 92. The control module 30 could also be integrated into other accessories used with the endoscope.

Figure 7:
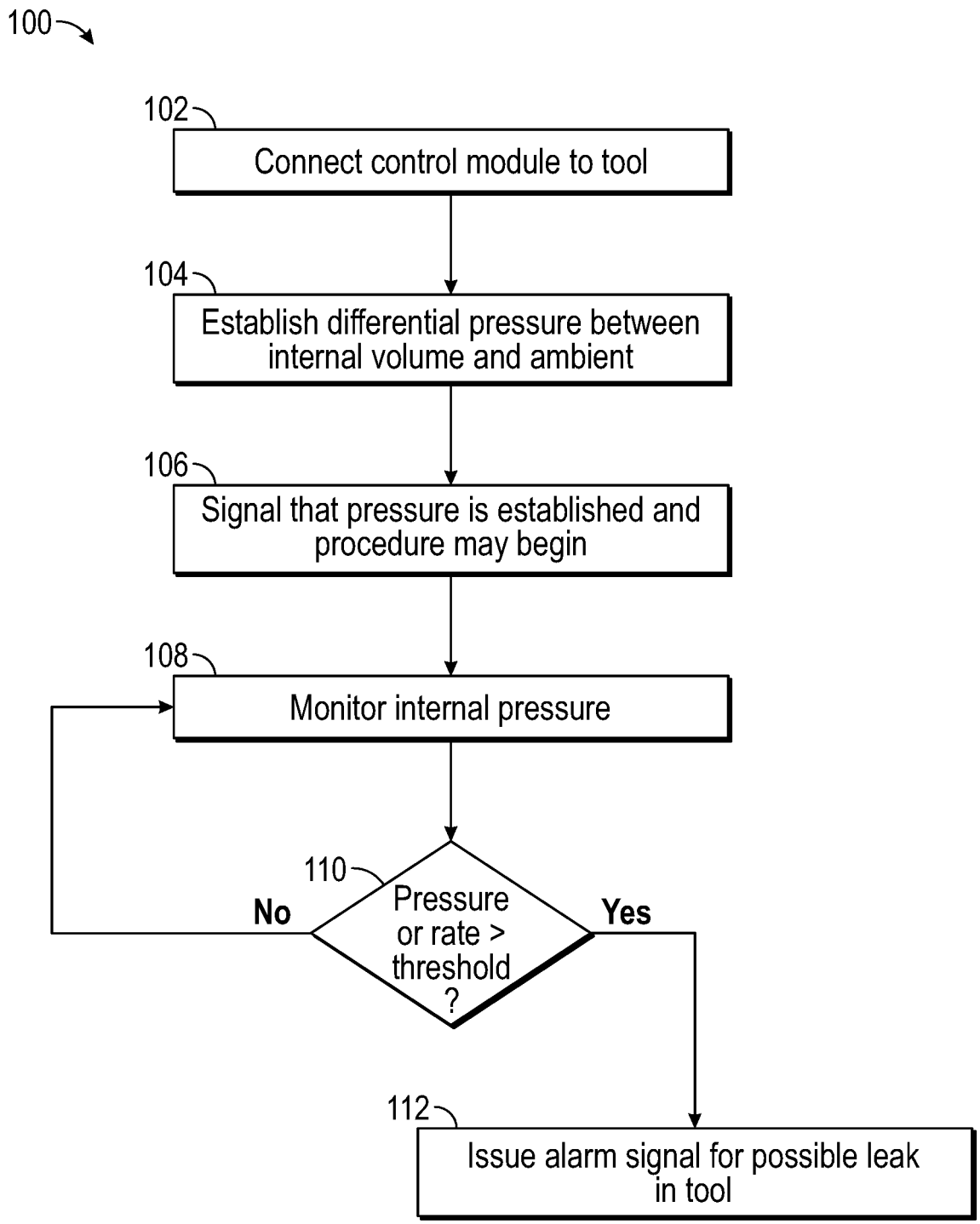
FIG. 7 is a flowchart diagram of a method for monitoring differential pressure in a tool to detect a leak, using the devices illustrated in FIGS. 1-6.

FIG. 7 is a flowchart diagram 100 of a method for monitoring differential pressure in a tool to detect a leak, using the devices illustrated in FIGS. 1-6. At step 102, the pressure monitoring control module 30 is connected to the tool 2 such that an internal volume of the control module 30 is in fluid communication with an internal volume of the tool 2 to create a combined internal volume. The control module 30 can be directly mounted upon the tool 2, or the control module 30 can be located remote from the tool 2 and connected with the hose 80.

At step 104, a pressure differential is established between the combined internal volume and the ambient pressure outside the tool 2 and the module 30. If an external pumping device is used, the pumping device can be switched on and off in a normal manner. If the active version of the control module 30 is used, a start button can be provided on the control module 30, or a start signal can be provided from a computer in the procedure room if so connected. At step 106, a signal is issued by the control module 30 indicating that the differential pressure has been established. The signal can be a solid green display of the LED 44 on the control module 30, or an audible tone, or any sort of signal can be communicated to the computer in the procedure room. Also at the step 106, the baseline or starting pressure is stored for usage during the monitoring phase. In the example discussed earlier, the baseline pressure after establishing the differential pressure is 10 psi absolute. As discussed, the baseline pressure can be any suitable value that is different from the ambient pressure outside the tool 2 and control module 30—where the internal pressure can be higher or lower than the external pressure.

At step 108, the tool 2 is in use (e.g. an endoscope being used by a physician to perform a procedure on a patient) and the pressure in the combined internal volume is continuously monitored by the control module 30 using the pressure sensor module 48. At decision point 110, the control module 30 monitors both the change in the internal pressure itself and the rate of change of pressure, and can issue an alarm if either of these parameters exceeds a predetermined threshold. For example, a pressure rate of change greater than 0.5 psi/minute can trigger an alarm. Also, if the baseline pressure is 10 psi, then a pressure sensor reading greater than 11 psi (change from baseline>1 psi) can trigger an alarm. The alarm thresholds listed here are merely exemplary. Thresholds can be configured based on the exact type of endoscope being used and procedure being performed. Threshold values can be configured by communication from a procedure room computer to the control module 30, or configured directly in the control module 30.

When no alarm condition is detected at the decision point 110, the process loops back to the step 108 to continue monitoring internal pressure. When an alarm condition is detected at the decision point 110, an alarm is issued at step 112 indicating a possible leak in the tool 2. The alarm can be any combination of a change in the LED 44 (change of color, a flashing code, etc.), an audible alarm, and/or any signal that can be displayed by a procedure room computer system based on an alarm signal from the control module 30. The alarm can be silenced by the tool operator if so desired. The operator may also choose to restart pressure monitoring after an alarm, beginning with re-establishment of the differential pressure.

Figure 8:
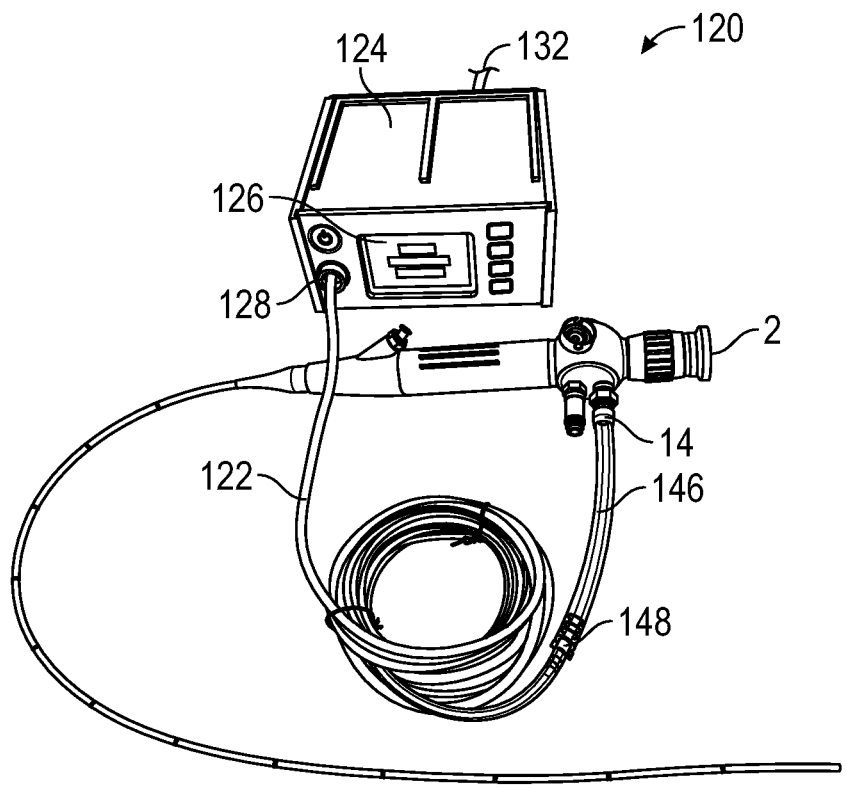
FIG. 8 is an illustration of a second embodiment of the pressure monitoring control module according to the invention located remotely from an endoscope and connected to the endoscope by a hose.
Figure 9:
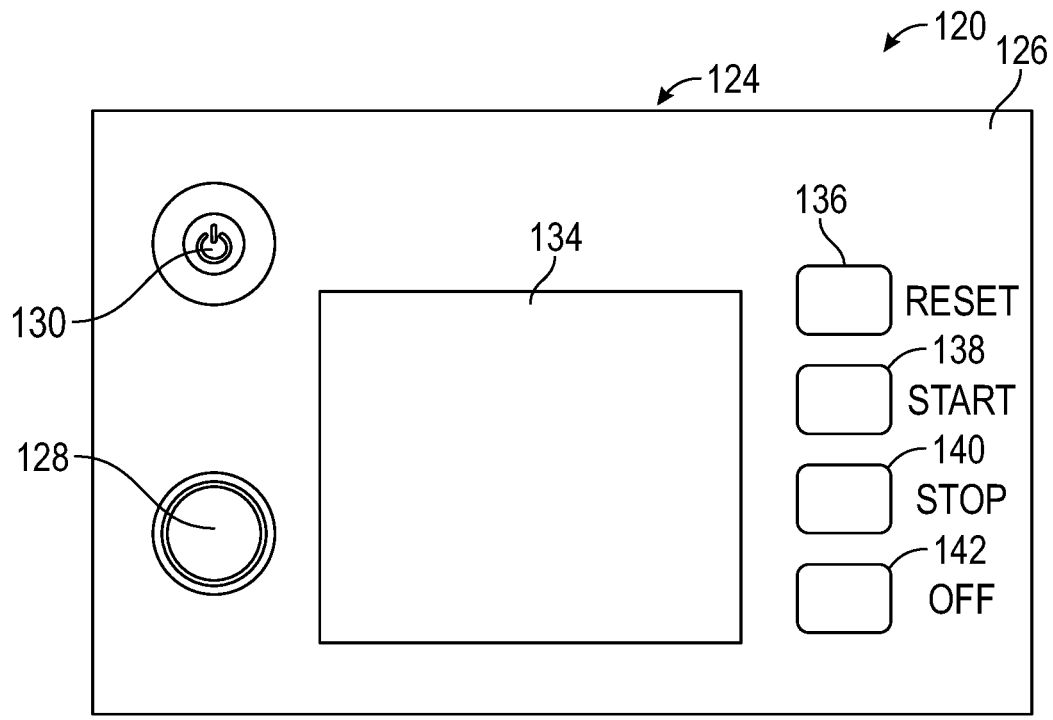
FIG. 9 is a front elevation view of the control panel of the control module shown in FIG. 8.

A second embodiment of the pressure monitoring control module according to the invention is shown in FIGS. 8-10B. Referring to FIGS. 8 and 9, a pressure monitoring control module 120 is located remotely from a tool 2 (endoscope) and is releasably connected to the endoscope by a disposable or reusable hose 122 with a filter. The control module 120 includes a housing 124 having a front wall configured as a control panel 126. One end of the hose 122 is connected to an outlet port 128 provided at the lower left in the control panel 126 and an opposite end of the hose is connected to a pressure port 14 of the endoscope 2. The differential pressure created by the control module 120 is communicated to the endoscope 2 via the hose 122. The hose 122 can be very small in diameter, as volume flow rate through the hose is not an important factor.

The control panel 126 of the control module 120 is shown in more detail in FIG. 9. An ON/OFF push button power switch 130 provided at the upper left in the control panel 126 switches electrical power provided to the control module 120 via a power cord 132 (FIG. 8) at the back of the control module. The power cord 132 can be plugged into a conventional electrical outlet (not shown) to receive AC power required to energize the components in the housing 124. A display panel 134 is positioned centrally in the control panel 126. The display panel 134 displays messages, such as instructions, status information and alarms, for the operator and can function as an input device used by the operator for operating various functions of the control module 120. For example, the display panel 134 can be a liquid crystal display (LCD) or a light emitting diode (LED) panel and can include a touchscreen capability. To the right of the display panel 134 is a vertical array of lighted push button switches that can be used by the operator to select operating modes of the control module 120 when performing the method shown in FIG. 7. Actuation of a START switch 138 initiates the generation of the differential pressure and the monitoring of the pressure in the combined internal volume during a medical procedure using the endoscope 2. Actuation of a STOP switch 140 terminates the method without releasing the differential pressure. Actuation of a RESET switch 136 during performance of the method restarts the method. Actuation of an OFF switch 142 terminates the method and releases the differential pressure. In the alternative, actuation of the STOP switch 140 and/or actuation of the RESET switch 142 could also release the differential pressure.

Figure 10A:
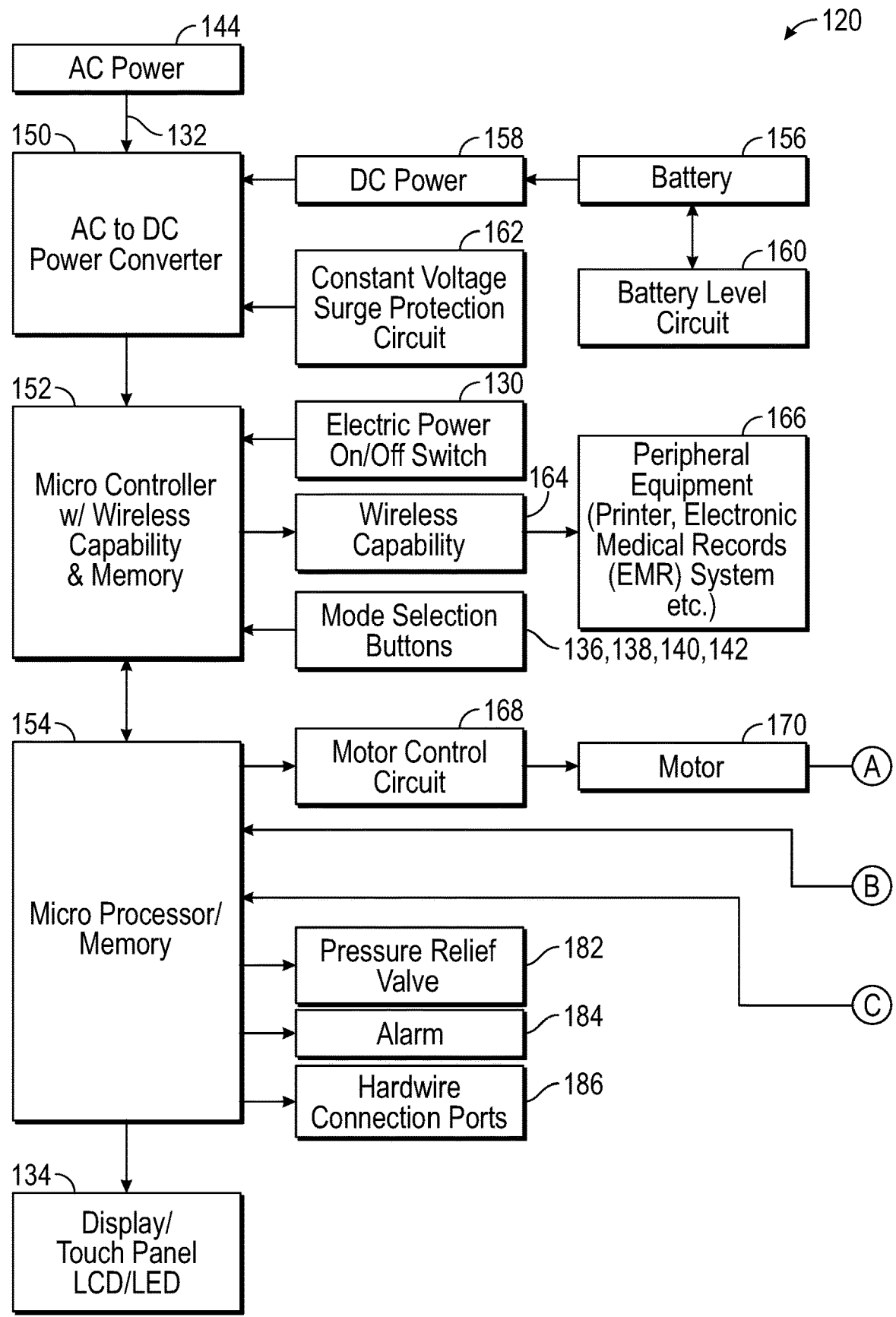
FIGS. 10A and 10B are a schematic block diagram of the interconnection of the components included in the control module shown in FIGS. 8 and 9.
Figure 10B:
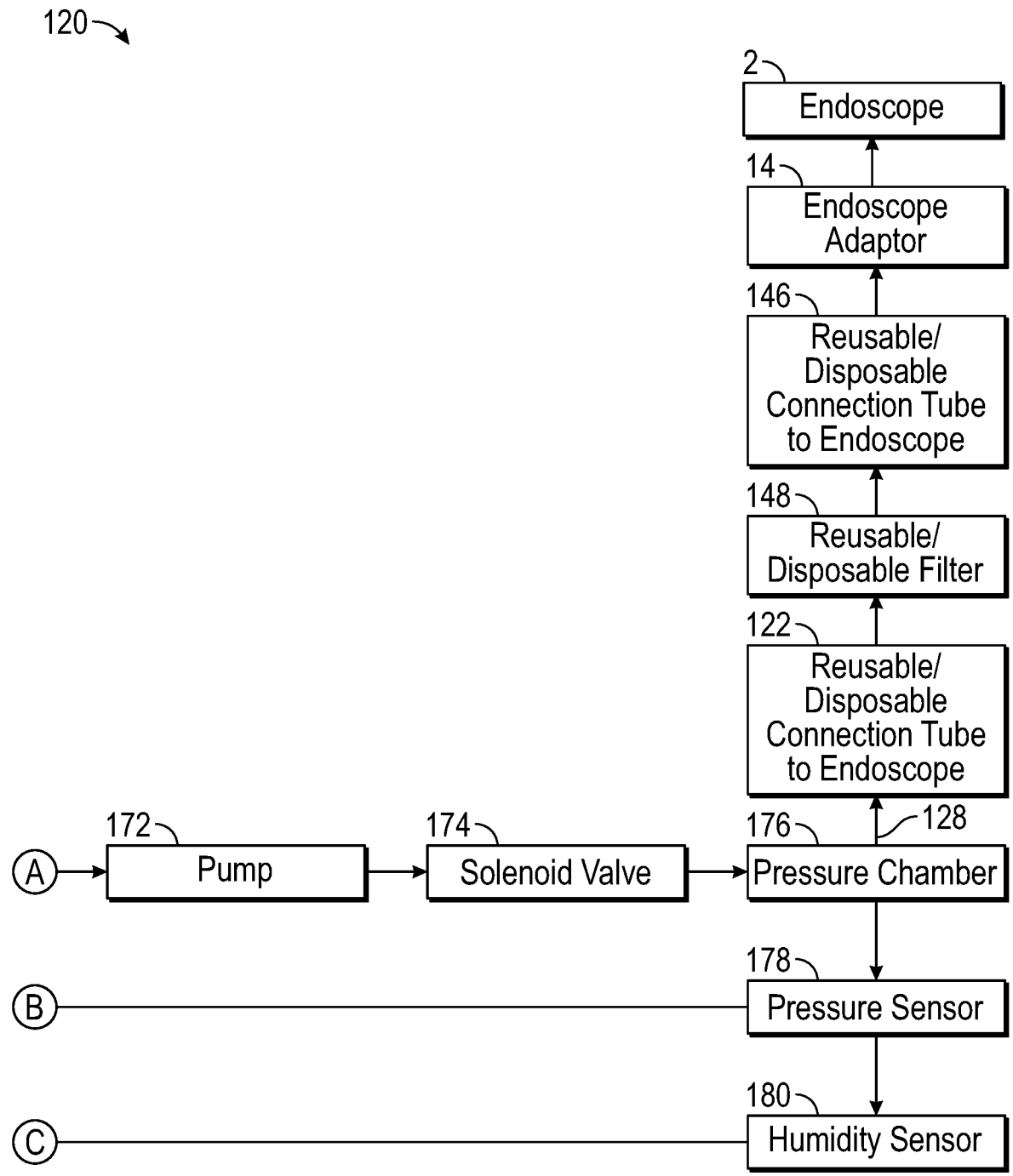

FIGS. 10A and 10B are a schematic block diagram of the interconnection of the components included in the control module 120 shown in FIGS. 8 and 9 as well as the connections with external components used during performance of the method according to the invention. The views are linked at "A", "B" and "C". The external components include an AC power source 144 that can be a conventional electrical outlet into which the power cord 132 is plugged. Other external components are the endoscope 2 with the pressure port (endoscope adapter) 14 connected to a reusable or disposable connection tube 146 (FIG. 8). The tube 146 is connected to an outlet end of the hose 122 through a reusable or disposable filter provided in an optional filter coupling device 148 (FIG. 8). The opposite end of the hose 122 is connected to the outlet port 128.

The internal components of the control module 120 are positioned inside the housing 124 (FIG. 8). An input of an AC to DC power converter 150 is connected to the power cord 132 to receive the AC power. An output of the converter 150 is connected to provide DC power at a suitable voltage to a microcontroller 152 and other components of the control module 120. The microcontroller 152 is connected to a microprocessor with memory 154 that is connected to the display panel 134. A battery 156 is connected to the converter 150 through a DC power circuit 158 to provide electrical power when the AC power source 144 is interrupted or otherwise not available. The circuit 158 also recharges the battery 156 from the converter 150 under control of a battery level circuit 160. A constant voltage surge protect circuit 162 is connected to the converter 150 to protect the control module components from AC power surges.

The ON/OFF power switch 130, the RESET switch 136, the START switch 138, the STOP switch 140 and the OFF switch 142 are inputs to the microcontroller 152. A wireless communication circuit 164 is connected to the microcontroller 152 for communication with peripheral equipment 166 such as printers and electronic medical records systems, etc.

A motor control circuit 168 is connected between the microprocessor 154 and an electric motor 170 that drives a pump 172. An outlet of the pump 172 is connected through a solenoid valve 174 to an inlet of a pressure chamber 176. The microprocessor 154 and the motor control circuit 168 operate the motor 170 to cause the pump 172 to generate a predetermined differential pressure in the pressure chamber 176. The motor 170 can be operated to generate both negative and positive pressure differentials. The microprocessor 154 controls the solenoid valve 174 to maintain and release the differential pressure as required by the method. An outlet of the pressure chamber 176 is connected to the outlet port 128. As described above in connection with the first embodiment, sensors are used to detect and report various conditions associated with the pressure chamber 176. For example, a pressure sensor 178 detects the differential pressure in the pressure chamber 176, representing the combined internal volume pressure, and sends a pressure signal to the microprocessor 154 for operating the motor control circuit 168 and generating alarm signals and messages. A humidity sensor 180 detects the humidity level in the pressure chamber 176, representing the combined internal volume humidity, and sends a humidity signal to the microprocessor 154 for operating the motor control circuit 168 and generating alarm signals and messages.

Also connected to the microprocessor 154 are a pressure relief valve 182, an alarm 184 and at least one hardware connection port 186. The pressure relief valve 182 is operated to relieve the differential pressure at a connection in the fluid communication path between the pump outlet and the outlet port 128. The alarm 184 can generate any one or combination of a visual signal (change of color, a flashing code, etc.), an audible alarm, and/or any signal that can be displayed by a procedure room computer system based on an alarm signal from the microprocessor 154. Among the alarm signals are signals based on outputs from the pressure sensor 178 and the humidity sensor 180. The at least one hardware connection port 186 can be, for example, a USB port in the rear wall of the housing 124 for communication with a device such as a printer or a computer.

The apparatus and the method disclosed above for monitoring differential pressure fulfill the need for real-time leak detection in endoscopes and other tools. The various embodiments—including active, passive, tool-mounted and remote—offer great flexibility in selecting a control module most suited to a particular application.

While a number of exemplary aspects and embodiments for a pressure differential monitoring leak testing device have been discussed above, those of skill in the art will recognize modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A leak-detecting apparatus that monitors a differential pressure in a closed-cavity tool during use of the tool to perform a procedure, the apparatus comprising:
   a motor driving a pump, the pump having an outlet;
   a pressure chamber having an inlet and an outlet, the outlet of the pump being connected to the inlet of the pressure chamber, the pressure chamber having an internal volume such that when the tool is coupled to the outlet of the pressure chamber an internal volume of the tool is in fluid communication with the internal volume of the pressure chamber thereby forming a combined internal volume;
   wherein the pump is adapted to change air pressure inside the combined internal volume to establish a baseline pressure inside the combined internal volume that is lower than an ambient pressure outside the tool;
   a pressure sensor monitoring the air pressure in the combined internal volume;
   a processor connected to the motor and the pressure sensor, the processor configured to perform a method of establishing the baseline pressure using the pump by operating the motor and monitoring the air pressure inside the combined internal volume using the pressure sensor during the use of the tool to perform the procedure; and
   a start switch, a stop switch and an off switch, each of the switches being in communication with the processor, wherein actuation of the start switch initiates the processor to perform the method, actuation of the stop switch terminates the operation of the motor and terminates the monitoring of the air pressure, without releasing the air pressure in the combined internal volume, and actuation of the off switch terminates the method and releases the air pressure in the combined internal volume.

2. The apparatus according to claim 1 including a reset switch in communication with the processor, wherein actuation of the reset switch restarts the method.

3. The apparatus according to claim 1 wherein the baseline pressure is 20-40% lower than the ambient pressure outside the tool.

4. The apparatus according to claim 1 including an alarm connected to the processor and wherein the processor issues from the alarm an alarm signal indicating a possible leak in the tool if the air pressure inside the combined internal volume changes from the baseline pressure by more than a threshold amount or a rate of change of the air pressure inside the combined internal volume exceeds a rate threshold.

5. The apparatus according to claim 4 including a humidity sensor or a moisture sensor connected to the processor and wherein the processor issues from the alarm another alarm signal upon detection of moisture or a change of humidity in the combined internal volume.

6. The apparatus according to claim 1 including at least one communication channel enabling electronic communication between the processor and peripheral equipment.

7. The apparatus according to claim 1 including a hose connected to the outlet of the pressure chamber, a tube coupled to the tool, and the hose and the tube being connected through a filter.

8. The apparatus according to claim 1 wherein the processor includes a microcontroller connected to a microprocessor with a memory, the microcontroller being connected to each of the switches, and the microprocessor being connected to the motor by a motor control circuit.

9. The apparatus according to claim 1 wherein the tool is a medical endoscope and the procedure is a medical procedure using the endoscope.

10. The apparatus according to claim 1 including a display panel connected to the processor and displaying messages to a user of the apparatus including signaling when the baseline pressure is established.

11. The apparatus according to claim 10 including a humidity sensor connected to the processor and monitoring a humidity inside the combined internal volume, wherein the processor signals on the display panel when the monitored humidity differs from a baseline humidity previously measured in the combined internal volume.

12. The apparatus according to claim 1 including a valve connected between the outlet of the pump and the inlet of the pressure chamber, the valve being controlled by the processor to establish fluid communication between the pump and the combined internal volume during the changing of the air pressure inside the combined internal volume by the pump and to block fluid communication between the pump and the combined internal volume during the operation of the tool.

13. A method for detecting a leak in a medical endoscope during operation of the endoscope to perform a medical procedure, the method comprising the steps of:
    providing the leak-detecting apparatus according to claim 1;
    releasably coupling the apparatus to the endoscope such that an internal volume of the endoscope is in fluid communication with the internal volume of the pressure chamber thereby forming the combined internal volume;
    changing the air pressure inside the combined internal volume using the pump to establish the baseline pressure inside the combined internal volume that is lower than an ambient pressure outside the endoscope;
    monitoring the air pressure inside the combined internal volume during operation of the endoscope to perform the medical procedure using the pressure sensor connected to the processor in the housing; and
    issuing an alarm signal indicating a possible leak in the endoscope when the air pressure inside the combined internal volume changes from the baseline pressure by more than a threshold amount or a rate of change of the air pressure inside the combined internal volume exceeds a rate threshold.

14. The method according to claim 13 wherein the established baseline pressure inside the combined internal volume is 20-40% lower than the ambient pressure outside the endoscope.

15. The method according to claim 13 including monitoring a humidity inside the combined internal volume and signaling to a user of the endoscope when the humidity differs from a baseline humidity previously measured in the combined internal volume.

* * * * *